United States Patent [19]  [11] 4,304,935
Brammer-Petersen et al.  [45] Dec. 8, 1981

[54] PRODUCTION OF 1-PHENYL-3-CYANOUREAS

[75] Inventors: John V. Brammer-Petersen, Espergaerde, Denmark; Christer L. Hakanson; Per T. Lindgren, both of Helsingborg, Sweden

[73] Assignee: Rexolin Chemicals AB, Helsingborg, Sweden

[21] Appl. No.: 138,480

[22] Filed: Apr. 9, 1980

[51] Int. Cl.³ ............... C07C 127/19; C07C 127/15
[52] U.S. Cl. .................... 564/48; 564/52; 564/59
[58] Field of Search .............. 564/23, 48, 52, 59, 564/104, 105

[56] References Cited

U.S. PATENT DOCUMENTS 2,557,984  6/1951  Marsh et al. .................... 564/23
3,935,258  1/1976  Hempel et al. ................. 564/48 X
4,082,749  4/1978  Quadbeck-Seeger et al. ... 564/48 X
4,084,056  4/1978  Häkanson ........................ 560/29
4,098,788  7/1978  Crenshaw et al. ............. 564/23 X Primary Examiner—John Doll
Attorney, Agent, or Firm—P. M. Pippenger

[57] ABSTRACT

Disclosed herein is a method for producing 1-phenyl-3-cyanoureas with the general formula:

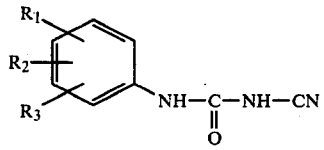

by reacting the corresponding benzamide with an alkali metal or alkaline earth metal hypohalite followed by reaction with cyanamide.

16 Claims, No Drawings

PRODUCTION OF 1-PHENYL-3-CYANOUREAS

BACKGROUND OF THE INVENTION

Phenylcyano ureas have been prepared heretofore by reacting a phenyl isocyanate with cyanamide. The general procedure is described by F. Kurzer, et al Org. Syn., Coll. Vol. IV, page 213. This procedure is also referred to at column 5, lines 33-41 of U.S. Pat. No. 4,098,788 and is exemplified at column 6, lines 5-30 of that patent. As discussed in U.S. Pat. No. 4,098,788, the 1-phenyl-3-cyanoureas are used in synthesizing certain quinazolines useful in treating hypertension.

Unfortunately, the phenyl isocyanates referred to above may, and frequently are, difficult to obtain. This problem is discussed in U.S. Pat. No. 4,084,056 at column 1, lines 40-52. As an alternate to phenyl isocyanates, U.S. Pat. No. 4,084,056 indicates that the corresponding benzamides can be treated with alkali metal hypochlorite to produce amines via the Hofmann reaction. However, rather than allowing the Hofmann reaction to go to completion, at an intermediate stage certain reactive intermediates (e.g., phenyl isocyanates of N-chlorobenzamide) are "trapped" by reaction with phenols to produce the desired carbamate esters. Use of N-chloro amides is a well known variant of the Hofmann reaction. For example, Elliott, J. Chem. Soc. 121, 202-9 (1922) prepared N-chlorobenzamide and reacted this with various nucleophiles to produce phenyl carbamates and ureas. Phenylcarbamate esters have also been prepared from benzamide using molecular halogen in alcohols in the presence of alkoxides or dry alkali carbonates. See Wallis et al, Organic Reactions, Vol. III, pages 267-306. These methods involve the use of molecular halogen and/or isolation of the free N-chlorobenzamide.

In summary, methods are known to modify the Hofmann reaction so as to "trap" the intermediate isocyanate with nucleophiles in the absence or presence of water and in ways which are generally practical. However, we are not aware of any instance where cyanamide or any derivative thereof has been used as the nucleophile.

Moreover, cyanamide is known to react with halogens and hypohalites to give unidentified, unstable and even explosive products. See Beilstein E II 3, page 64. While we have encountered no problems in the use of cyanamide, and this is unexpected, customary industrial precautions should be exercised in employing the invention.

DESCRIPTION OF THE INVENTION

The present invention is a process for preparing cyanourea compounds of formula I

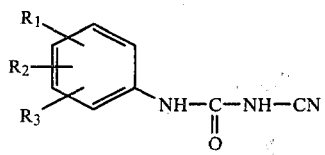

wherein $R_1$, $R_2$ and $R_3$ are independently selected from the group consisting of hydrogen, lower alkyl of 1-4 carbon atoms inclusive and lower alkoxy of 1-4 carbon atoms inclusive; which comprises the consecutive steps of;

(a) treating a benzamide of the formula II

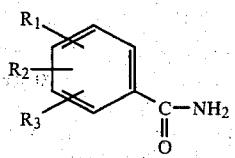

wherein $R_1$, $R_2$ and $R_3$ are as defined above with hypohalite ion; and (b) admixing the reaction mixture produced in (a) with cyanamide in the presence of a base.

It is to be understood that by the terms "lower alkyl" and "lower alkoxy", as used herein, it is meant that the carbon chain which comprises these groups include both straight and branched carbon radicals of 1 to 4 carbon atoms inclusive. Exemplary of these carbon chain radicals are methyl, ethyl, propyl, isopropyl, 1-butyl, 1-methylpropyl, 2-methylpropyl, and tert.-butyl.

By the term "independently selected", as used herein, it is meant that the $R_1$, $R_2$ and $R_3$ substituents may or may not be identical.

It is also advantageous, in conjunction with hypohalite treatment of the benzamide, or in the second stage of the synthesis, to add a water-miscible solvent which improves the solubility of the reactants in the reaction mixture. Lower alcohols, such as methanol or ethanol, as well as glycols, are particularly suitable for this purpose.

In treating the benzamide, the hypohalite anion is provided by an alkali metal hypohalite or alkaline earth metal hypohalite. Preferably, an alkali metal hypochlorite, e.g., sodium or potassium hypochlorite is employed. The sodium hypochlorite is available commercially as an aqueous solution prepared by dissolving chlorine in aqueous sodium hydroxide. A suitable alkaline earth hypochlorite is calcium hypochlorite. The hypohalite compounds are used in the form of aqueous solutions.

In carrying out the synthesis, the cyanamide is generally added to the hypohalite-treated benzamide as an aqueous solution in the presence of a base e.g., sodium hydroxide. It is also possible, however, to add the hypohalite-treated benzamide to aqueous solutions of cyanamide, slowly and with stirring.

Step (a) in the synthesis is appropriately carried out at a temperature of between $-20°$ C. and $20°$ C., and preferably $-10°$ to $10°$ C. In carrying out step (b), the reaction is exothermic and can be allowed to exceed $20°$ C. and generally will fall in the range of $20°-65°$ C. Following completion of the reaction, the reaction mixture is acidified (e.g., pH less than 5) to separate the 1-phenyl-3-cyanourea.

In carrying out the above reaction sequence the cyanamide/benzamide molar ratio is from about 1 to about 5 and preferably from about to about 2. An excess of cyanamide is preferred to minimize side reactions. The benzamide/alkali metal hypohalite or alkaline earth hypohalite molar ratio is from about 0.8 to about 1.2 and preferably is about 1.

Where cyanamide is added to the hypohalite-treated benzamide in the presence of a base (e.g., NaOH), from about 1 to 2 moles of base can be employed for each mol of benzamide. Generally, the amount of base does not exceed about one mol for each mol of cyanamide. The base should not be added later than at an early stage in the exothermic reaction with cyanamide.

EXAMPLE 1

Preparation of 1-(3,4-Dimethoxyphenyl)-3-cyanourea 7.25 g, (0.04 mole) of 3,4-dimethoxybenzamide was added to 40 ml of methanol. A mixture of 3.14 g, (0.038 mole) of 48% sodium hydroxide solution and 22 ml, (0.04 mole) sodium hypochlorite solution was added with stirring while the temperature was kept at 0° C. to +2° C. by external cooling. Water (13 ml) was added at +2° C.−+5° C. until a clear solution was obtained. The solution was thereupon stirred for about ten minutes at +2° C.−+3° C . A 50% solution of cyanamide (5.05 g, 0.06 mole) in water was rapidly added while stirring. After a few minutes an exothermic reaction started whereby the temperature slowly rose to +33° C. and the solution became darker. The pH of the solution decreased from 12 to 10. The solution was kept at around 33° C. for about 30 minutes. Thereafter, the temperature was reduced to about 15° C. and concentrated hydrochloric acid was added until the pH of the reaction mixture was about 3. Acidification caused greyish, finely divided crystals of 1-(3,4-dimethoxyphenyl)-3-cyanourea to form and stirring was continued at 15° C. for about 30 minutes. The crystals were filtrated, washed with water and dried. The dried crystals weighed 8.0 g (90.4% yield). The melting point was 147° C.−150° C. and the mol weight by sodium hydroxide titration was 100.8% of the theoretical. Pure material, obtained by crystallization from acetonitrile, has a melting point of 154° C.−156° C.

EXAMPLE 2

Preparation of 1-Phenyl-3-cyanourea

The title compound was produced by following the procedure of Example 1 but employing an equimolar amount of benzamide in place of 3,4-Dimethoxybenzamide. Yield of crude 1-Phenyl-3-cyanourea: 81%. M.p. 120° C.−122° C. (dec.). Mol weight (by sodium hydroxide titration): 101.0% of theoretical.

EXAMPLE 3

Following the procedure of Example 1 but employing an equimolar amount of the benzamides listed below:
2-methylbenzamide,
3-methylbenzamide,
4-methylbenzamide,
3-n-butylbenzamide,
4-isopropylbenzamide,
2,4-dimethylbenzamide,
3,4-dimethylbenzamide,
2,3,4-trimethylbenzamide,
2-methoxybenzamide,
3-methoxybenzamide,
3-methoxybenzamide,
4-methoxybenzamide,
3-n-butoxybenzamide,
4-isopropoxybenzamide,
2,4-dimethoxybenzamide,
2,3,4-trimethoxybenzamide,
in place of 3,4-dimethoxybenzamide, the following cyanoureas can be produced respectively,
(a) 1-(2-methylphenyl)-3-cyanourea,
(b) 1-(3-methylphenyl)-3-cyanourea,
(c) 1-(4-methylphenyl)-3-cyanourea,
(d) 1-(3-n-butylphenyl)-3-cyanourea,
(e) 1-(4-isopropylphenyl)-3-cyanourea,
(f) 1-(2,4-dimethylphenyl)-3-cyanourea,
(g) 1-(3,4-dimethylphenyl)-3-cyanourea,
(h) 1-(2,3,4-trimethylphenyl)-3-3-cyanourea,
(i) 1-(2-methoxyphenyl)-3-cyanourea,
(j) 1-(3-methoxyphenyl)-3-cyanourea,
(k) 1-(4-methoxyphenyl)-3-cyanourea,
(l) 1-(3-n-butoxyphenyl)-3-cyanourea,
(m) 1-(4-isopropoxyphenyl)-3-cyanourea,
(n) 1-(2,4-dimethoxyphenyl)-3-cyanourea,
(o) 1-(2,3,4-trimethoxyphenyl)-3-cyanourea.

The preparations listed in this Example 3 have not been actually carried out but are logical extrapolations of the procedures set forth in Examples 1 and 2.

What is claimed is:

1. A process for preparing cyanourea compounds of formula I

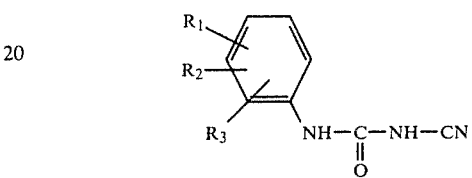

wherein $R_1$, $R_2$ and $R_3$ are independently selected from the group consisting of hydrogen, lower alkyl of 1 to 4 carbon atoms inclusive and lower alkoxy of 1 to 4 carbon atoms inclusive; which comprises the consecutive steps of:

(a) treating a benzamide of the formula II

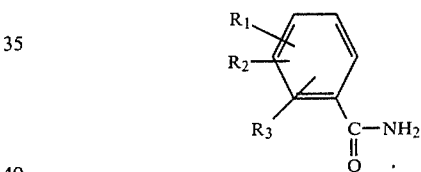

wherein $R_1$, $R_2$ and $R_3$ are as defined above with hypohalite ions; and (b) admixing the reaction mixture produced in (a) with a sufficient amount of cyanamide in the presence of a base, to provide a mole ratio of cyanamide to benzamide of from 1 to 5.

2. A process as in claim 1 wherein the benzamide is 3,4-dimethoxybenzamide.

3. A process as in claim 1 wherein the benzamide is 2,3,4-trimethoxybenzamide.

4. A process as in claim 1 wherein steps (a) and (b) are carried out in the presence of a water-miscible organic solvent.

5. A process as in claim 1 wherein the hypohalite ion is provided by sodium hypochlorite.

6. A process as in claim 1 wherein the hypochlorite ion is provided by calcium hypochlorite.

7. A process as in claim 1 wherein step (a) is conducted at a temperature of from −20° to 20° C.

8. A process as in claim 1 wherein step (a) is conducted at a temperature of from −10° to 10° C.

9. A process as in claim 1 wherein the base employed in step (b) is an alkali metal hydroxide.

10. A process as in claim 1 wherein the base employed in step (b) is sodium hydroxide.

11. A process as in claim 1 wherein the temperature of the reaction mixture in step (b) is from 20°−65° C.

12. A process as in claim 1 wherein the temperature of the reaction mixture in step (b) is allowed to exceed 20° C.

13. A process as in claim 1 wherein the cyanourea is isolated by acidifying the reaction mixture of step (b).

14. A process as in claim 1 wherein the approximately equimolar amounts of benzamide and cyanamide are employed.

15. A process as in claim 1 wherein an alkali metal or alkaline earth metal hypolite is employed in step (a) and the molar ratio of hypohalite to benzamide is from 0.8 to 1.2.

16. A process as in claim 4 wherein the organic solvent is methanol.

* * * * *